United States Patent [19]

Sturm

[11] 4,300,049
[45] Nov. 10, 1981

[54] DYNAMICALLY STANDARDIZED RADIANT ENERGY METHOD AND APPARATUS FOR PLURAL CHANNEL GAIN INDEPENDENT MATERIAL PROPERTY MEASUREMENT

[75] Inventor: Steven P. Sturm, Columbus, Ohio

[73] Assignee: AccuRay Corporation, Columbus, Ohio

[21] Appl. No.: 125,225

[22] Filed: Feb. 27, 1980

[51] Int. Cl.³ .......................... G01J 1/00; G01D 18/00
[52] U.S. Cl. .................................. 250/339; 250/252; 250/350
[58] Field of Search ............... 250/252, 308, 339, 340, 250/341, 349, 350, 351

[56] References Cited

U.S. PATENT DOCUMENTS

| | | | |
|---|---|---|---|
| 2,829,268 | 4/1958 | Chope | 250/252 |
| 2,951,161 | 8/1960 | Foster et al. | 250/308 |
| 3,405,268 | 10/1968 | Brunton | 250/339 |
| 3,803,414 | 4/1974 | Van Horne et al. | 250/341 |
| 3,851,175 | 11/1974 | Dahlin et al. | 250/339 |
| 3,957,372 | 5/1976 | Jowett et al. | 356/51 |
| 4,006,358 | 2/1977 | Howarth | 250/339 |
| 4,052,615 | 10/1977 | Cho | 250/341 |
| 4,057,734 | 11/1977 | Barringer | 250/345 |
| 4,085,326 | 4/1978 | Williams | 250/339 |
| 4,097,743 | 6/1978 | Carlson | 250/339 |

OTHER PUBLICATIONS

Sturm, S. "Correction for the Dynamic Effect of the Printed Pattern on the Substrate on Coating Measurements", Report No. 2660-C (unpublished) of AccuRay Corp. pp. 1 & 9-24.

*Primary Examiner*—Alfred E. Smith
*Assistant Examiner*—Janice A. Howell

*Attorney, Agent, or Firm*—C. Henry Peterson

[57] ABSTRACT

A method and apparatus for determining a property of a material (10) utilizes a source (28) of measuring radiation and reference radiation, a measuring information channel including a detector (30) for the measuring radiation, and a reference information channel including a detector (32) for the reference radiation. A channel-monitoring radiation is also produce. In a standardizing mode, a monitor-standardization response ($M_{11}$ or $R_{11}$) is derived from each of the two channels while passing monitoring radiation to both detectors and a source-standardization response ($M_{12}$ or $R_{12}$) is derived from each of the two channels while passing measuring radiation to the measuring detector and passing reference radiation to the reference detector. In an operating mode, an operation-monitoring response ($M_{21}$ or $R_{21}$) is derived from each of the two channels while passing monitoring radiation to both detectors and a material-condition response ($M_{22}$ or $R_{22}$) is derived from each of the two channels while directing source radiation into the material and passing to the respective measuring and reference detectors measuring and reference radiation that has interacted with the material. By responding to the monitor-standardization responses, the source-standardization responses, the operation-monitoring responses and the material-condition responses, there is produced a material property response (at 164 or 166) that is effectively standardized and substantially independent of gain changes occurring in either one or both of the measuring and reference information channels. The example shows the measurement of moisture content in a traveling sheet of paper with infrared radiation at $1.4\mu$, $1.8\mu$ and $1.9\mu$.

48 Claims, 4 Drawing Figures

DYNAMICALLY STANDARDIZED RADIANT ENERGY METHOD AND APPARATUS FOR PLURAL CHANNEL GAIN INDEPENDENT MATERIAL PROPERTY MEASUREMENT

TECHNICAL FIELD

This invention relates to methods and apparatus for determining a property of a material, utilizing a measuring radiation and a reference radiation. These radiations are detected by respective radiation detectors. Each detector is a component of an individual information channel. The material property is determined by appropriately processing the information supplied by the two channels under appropriate conditions.

More particularly this invention relates to such methods and apparatus wherein there is produced what is herein termed a channel-monitoring radiation, that is detected by both detectors when functioning in the operating mode and again when functioning in the alternative standardizing mode. The information provided in this manner is processed along with the information obtained by detecting the measuring and reference radiations in the operating mode and again in the alternative standardizing mode. As a result, there is produced a material property response that is effectively standardized and substantially independent of gain changes occurring in either one or both of the measuring and reference information channels.

While a great many applications and different embodiments are possible, the invention will be described and illustrated in the form of methods and apparatus using infrared radiation for determining the moisture content of paper as it is processed continuously by a paper making machine.

BACKGROUND ART

It is a commonplace procedure to determine a material property by detecting measuring and reference radiations that have been emitted, absorbed, transmitted or reflected by the material. The terms "measuring" radiation and "reference" radiation are used herein simply to distinguish between two radiations that interact with the material in a different way. One radiation may interact selectively with the material, while the other radiation may exhibit only a generalized interaction.

Some examples of selective interaction include molecular resonance absorption in the infrared region, color filtration in the visible region, and K-edge absorption in the X-ray region of the electromagnetic spectrum. Some examples of generalized, non-selective interactions include the absorption of infrared radiations having wavelengths that are spectrally removed from the absorption bands of the material being measured, the filtration of light with neutral-density filters, and the absorption of beta rays by various materials.

The moisture content of a continuously-produced sheet of paper is commonly inferred from measurements of infrared radiation that is generated by an infrared radiation source means on one side of the sheet, directed to pass through the paper, and detected on the opposite side of the sheet. The detected radiation is separated into two narrow bands of wavelengths, including a band around $1.9\mu$ that is herein termed a measuring radiation and a band around $1.8\mu$ or $1.7\mu$ that is herein termed a reference radiation. If it is desired to also measure the basis weight of the paper with the same instrument, an additional band of measuring radiation may also be separately detected as described in U.S. Pat. No. 3,405,268.

For various measurements, additional bands of reference radiations may be needed to correct for the effects of certain wavelength interactions with the microstructures of the material, and special wavelengths may be used to correct for the presence of certain ingredients or surface effects that exist in the material, for example, as described in U.S. Pat. No. 4,085,326.

It has generally been preferred to time-multiplex the measuring and reference radiations for alternate or sequential detection by a single detector in a single information channel, and to effectively compute the ratio M/R of the information channel response. This permits common-mode cancellation of many extraneous variables that influence the detected values of either radiation by itself. More-over, the apparently inevitable drifts that occur in the detector response can be made to appear as simple gain changes in the single information channel, and likewise cancel when the ratio is taken. However, such factors as shifts in the spectral content of the infrared radiation source, spectral shifts in one or both filter passbands, certain kinds of dirt accumulation on the windows over the source and detector, and certain electronic drifts do not admit of common-mode cancellation, and hence a standardization procedure is also required.

Standardization is commonly performed in a manner consistent with the law of Bouguer (sometimes referred to as the Lambert-Beer law of absorption)

$$I = I_o e^{-\mu x}$$

in the form $$\frac{I}{I_o} = e^{-\mu x} \quad (1)$$

Here $I_o$ represents the original intensity of radiation, and I represents its intensity after passing through a material having a mass per unit area x and an absorption coefficient $\mu$. The intensities I and $I_o$ are usually derived as voltages V and $V_o$ respectively, from the information channel containing the detector. Hence, equation (1) can be expressed as $$\frac{V}{V_o} = e^{-\mu x}$$

In the case of a dual-wavelength instrument, two such relationships are obtained $$\frac{V_M}{V_{Mo}} = e^{-\mu_M x} \text{ and } \frac{V_R}{V_{Ro}} = e^{-\mu_R x}$$

where the subscript M indicates that the voltage or absorption coefficient is associated with the measuring radiation and the subscript R indicates that the voltage or absorption coefficient is associated with the reference radiation.

Taking the ratio of the measuring and reference voltage responses results in a combined relationship $$\frac{\frac{V_M}{V_{Mo}}}{\frac{V_R}{V_{Ro}}} = \frac{V_M V_{Ro}}{V_{Mo} V_R} = e^{(\mu R - \mu M)x}$$

when x = o, $$\frac{V_M V_{Ro}}{V_{Mo} V_R} = 1.$$

The condition x=o is achieved, or simulated, by removing the material from between the source and detector, or by moving the source and detector to an off-sheet position, or by inserting a standardizing flag between the material and the source and detector, as variously described in U.S. Pat. Nos. 2,829,268, 2,951,161 and 3,803,414 and in 4,085,326 supra. The detector then receives, from the source, radiation that has not interacted with the material, and the instrument is enabled to restore its calibrated accuracy.

The standardization procedure ensures that suitably current and updated values for the quantities $V_{Mo}$ and $V_{Ro}$ (voltages or other forms of response values representing the original intensities of the measuring and reference radiations from the source) are available. These values may be placed in relatively long term storage (between standardization periods), for example, in a computer memory. They may then be used each time a material property (x) value is to be computed from the current measuring and reference response voltages $V_M$ and $V_R$ obtained while the material is being measured. Alternately the $V_{Mo}$ value can be set equal to the $V_{Ro}$ value on standardization, and their proper mutual relationship maintained, by long-term storage of a gain factor, as described, for example, in U.S. Pat. No. 4,085,326 supra.

In some cases the values $V_{Ro}$ and $V_{Mo}$ may be derived in a simulated fashion by using a radiation chopper to direct the radiation along a reference path, alternately with its direction along the measuring path, and utilizing short-term storage of the signals during portions of the revolution time of the chopper, as described, for example, in U.S. Pat. Nos. 3,957,372 and 4,097,743. This allows some compensation where certain errors exist and can become serious enough to need correction in a time period shorter than the normal standardization interval. However, it can also introduce new sources of error, due to possible extraneous variables associated with the reference path, that would not otherwise be encountered.

In the single-detector, dual-wavelength multiplex system, the detector "sees" the material being measured, first as it is illuminated by the reference radiation, next as it is illuminated by the measuring radiation, then again as illuminated by the reference radiation, and so on in a continuous, alternating series. When the instrument is used to measure a fast-traveling material, the material moves an appreciable distance in the time required for the switch from reference radiation to measuring radiation and from measuring radiation to reference radiation. Hence, the detector sees a series of spots on the material, with alternate spots actually or effectively illuminated by the reference radiation, and with the other spots actually or effectively illuminated by the measuring radiation. These spots may overlap to a greater or lesser extent, or they may not overlap at all, depending on the rate of movement of the material relative to the rate and manner of switching back and forth between measuring and reference radiations.

The responses of the information channel (containing the detector) to the measuring radiation-illuminated spots are separately averaged, or one or both are placed in relatively short-term storage, for comparison, usually by effectively taking the ratio M/R of the measuring and reference response values. The fact that the spots effectively illuminated by the measuring and reference radiations generally exhibit at least slightly different values of the property being measured (or of an interfering property) is not of any consequence ordinarily. Time averaging of the channel responses is used and chopping of the radiations from the source is generally necessary in any case involving radiations such as infrared in order to avoid the effects of changing ambient radiation.

There are, however, situations where special provisions have been necessary to avoid substantial errors that could otherwise arise from the use of the "two-spot" or plural spot method of measurement. The thickness of a polyethylene coating on paper is commonly measured by detecting reference radiation and measuring radiation reflected from the interface between the paper and the polyethylene. However, in one case the paper was imprinted with printing ink, applied in a repetitive pattern along the length of the traveling sheet, before the polyethylene coating was applied. The printing ink was an effective absorber for the infrared radiation wavelengths used. It was found that at certain line speeds particular phase relationships developed between the moving pattern of printing on the paper and the alternation of the reference and measuring wavelengths received by the detector, causing the polyethylene thickness measurements to substantially deteriorate.

To correct the measurements, an auxiliary band of wavelengths (e.g., around 1.4$\mu$), herein termed a "formation-monitoring radiation" was used together with an auxiliary second radiation detector that is herein termed a "formation detector". Now when a spot of reference radiation was directed into the material, the spot on the material was simultaneously illuminated with the formation-monitoring radiation. Similarly when the spot of measuring radiation was directed into the material, this spot on the material was likewise simultaneously illuminated also with the formation-monitoring radiation.

The principal radiation detector was equipped with a filter that substantially prevented the formation-monitoring radiation from reaching it. However, the principal detector still received the reference and measuring radiations alternately, and hence functioned in the same manner as before. The auxiliary formation detector was equipped with a filter that pevented the reference radiation and the measuring radiation from reaching it. However, when the principal detector received a pulse of reference radiation from the material, the formation detector received a pulse of formation-monitoring radiation, at the same instant and from the same illuminated spot on the material. Likewise, when the principal detector received a pulse of measuring radiation from the material, the formation detector received a pulse of formation-monitoring radiation, at the same instant and from the same spot on the material that provided the measuring radiation pulse.

The auxiliary information channel containing the formation detector provided a response $F_M$ to the formation-monitoring radiation arriving simultaneously with the arrival of the measuring radiation at the principal detector. The formation detector also provided a response $F_R$ to the formation-monitoring radiation arriving simultaneously with the arrival of the reference radiation at the principal detector. Hence the ratio $F_M/F_R$ provided a measure of the degree of change that took place in the interfering property (the amount and kind of printing ink present to absorb the measuring and reference radiations) during the time interval between the detection of the measuring and reference radiation pulses from the material. The ratio $F_M/F_R$ could then be used to correct the ratio R/M of the reference and measuring responses in accordance with $$\frac{R\,F_M}{F_R\,M}$$

or in accordance with the analog computation actually used $$\frac{\frac{R}{F_R} - \frac{M}{F_M}}{\frac{M}{F_M}} = \frac{R\,F_M}{F_R\,M} - 1$$

in a manner somewhat similar to that described in U.S. Pat. No. 4,085,326 supra.

It is also a commonplace procedure to detect the measuring radiation and the reference radiation with separate detectors, in separate information channels. In a few cases this is essential because the characteristics of the radiations, and the necessary structures of the detectors, are markedly different. A system using two detectors in this manner has been perceived to have a theoretical advantage, in that it provides a "single spot" measurement, at least to the extent that the measuring radiation pulses and the reference radiation pulses can be detected at the same instant in time as well as separately. This system also should have no difficulties with the printing ink application just described. In applications such as the measurement of moisture in heavy, highly non-uniform paper board, for example, using infrared radiation, it should reduce the effects of non-linear averaging and noise, thereby reducing the averaging time required for measurements to a desired degree of resolution.

However, the detectors used in such applications, and other elements of the information channels, are subject to short-term drifts and instabilities that make them respond differently, at different times and in an unpredictable way, to corresponding radiation stimuli. When one or both channels exhibit response changes or response components that have no counterpart in the response of the other channel, there is no common-mode cancellation of their extrinsic effects on the measurement, as is the case with the dual-wavelength, single-detector system. These problems have so far prevented many of the most attractive theoretical benefits of the dual-detector, separate measuring and reference channel systems from being realized.

Where these systems have been used, in addition to the usual standardization provisions, some rather complex arrangements have been made to slow down and-/or minimize the rate of drift in the detectors, by cryogenic gas or thermoelectric cooling, close temperature regulation of the detectors and other information-channel components to a tenth of a degree or so, and prevention of sudden and/or large changes in the intensity of the radiation falling on the detectors. More frequent standardization has been used to prevent the errors that do occur from becoming too large before they are corrected, say, each time the detectors are scanned across the width of a traveling paper sheet.

Additional steps in the standardization procedure have been added, including the insertion of internal standard radiation absorbers (filters) both to simulate the effect of a predetermined change in the basis weight (mass per unit area) of the sheet and to simulate a predetermined change in its moisture content. These standards may allow the extent of the existing errors to be computed or mathematically stated, and the instrument readings corrected, in a manner such as those described, for example, in U.S. Pat. Nos. 3,851,175 and 4,006,358. The effectiveness of such techniques do depend, however, on how well the constancy of the filters, and the precision of the mechanical filter insertion mechanisms, can be maintained. This can be very difficult in the hostile environments to which many industrial instruments must necessarily be subjected.

As shown by U.S. Pat. No. 4,057,734, it is known to use a spectrometric instrument for detecting gases such as sulfur dioxide in the atmosphere by measuring the spectra of light reflected from the earth that has traversed the atmosphere. A beam of this light is split by a beam splitter into two parts that are passed through respective measuring and reference wavelength band pass filters to respective measuring and reference radiation detectors in two separate information channels. The instrument contains an internal radiation source for producing a second beam of radiation that is herein termed channel-monitoring radiation.

A radiation chopper is arranged to periodically substitute the internally generated second beam for the first beam whose spectra are being measured. During the substitution periods the measuring radiation wavelengths contained in the channel-monitoring radiation beams are passed to the measuring detector, and the reference wavelengths contained in the channel-monitoring radiation beam are passed to the reference detector. At this time an automatic gain control (AGC) loop adjusts the gain in the measuring information channel to make its output equal to that from the reference channel. In another position of the chopper, it blocks both beams, and another control loop adds or subtracts a d.c. voltage in the measuring channel so that the dark current signal levels are equal in the two channels. In still another position of the chopper, the channel-monitoring beam of radiation is passed through a filter, such as a cell containing a sample of the gas that is being measured. The difference between the signals obtained from the two channels at this time is indicative of the sensitivity of the spectrometer, and may be used to automatically maintain the sensitivity at a constant level.

It was suggested that instead of using AGC feedback loops the outputs of the photodetectors could be converted to digital signals and the unbalance of the detectors could be compensated using conventional digital computing techniques. The instrument could be used to measure phenols in a water supply using the ultraviolet absorption bands of phenols in water. It could be used to measure gases present in a smoke stack by the absorption of a beam of light passed through the stack. To measure the fluorescence of materials in sunlight, or for sensing gases using the reflected solar spectrum, the internal channel-monitoring radiation source is replaced by a light pipe of fiber optics to introduce light from the sky into the spectrometer. In the latter two embodiments, the radiations from the measuring and reference radiation source (in this case, the sun) are passed to the detector through two paths alternately, the first path being the path through the material to be measured and the second being a reference path, in an arrangement similar to that of U.S. Pat. Nos. 3,957,372 and 4,097,743 supra.

DISCLOSURE OF INVENTION

In accordance with this invention, there is provided a method and means for determining a property of a material utilizing or comprising source means for producing source radiation including measuring radiation and reference radiation, a measuring information channel including a detector for the measuring radiation, and a reference information channel including a detector for the reference radiation, the source means and the information channels being utilized in both an operating mode and an alternative standardizing mode, and further comprising the method steps and means for producing a channel-monitoring radiation; in the standardizing mode, deriving a monitor-standardization response from each of the two channels while passing monitoring radiation to both detectors; in the standardizing mode, deriving a source-standardization response from each of the two channels while passing measuring radiation to the measuring detector and passing reference radiation to the reference detector; in the operating mode, deriving an operation-monitoring response from each of the two channels while passing monitoring radiation to both detectors; in the operating mode, deriving a material-condition response from each of the two channels while directing source radiation into the material, and passing to the respective measuring and reference detectors measuring and reference radiation that has interacted with the material, and responding to the monitor-standardization responses, the source-standardization responses, the operation-monitoring responses and the material-condition responses so as to produce a material property response that is effectively standardized and substantially independent of gain changes occurring in either one or both of the measuring and reference information channels.

The channel-monitoring radiation may be directed into the material in the operating mode, and the operation-monitoring responses may be derived in response to channel-monitoring radiation that is received by the detectors from the material.

The channel-monitoring radiation may be directed into the material from one side thereof and the detectors may receive the monitoring radiation from the opposite side, or the monitoring radiation reflected from the material may be detected on the same side.

Typically the channel-monitoring radiation is produced by the source means that produces the source radiation.

The measuring and reference radiation, that is passed to the respective measuring and reference detectors in order to derive the material-condition responses, may be radiation that has interacted with the material in substantially the same portion thereof.

Typically the channel-monitoring radiation is directed into the material in the operating mode, and the operation-monitoring responses are derived in response to monitoring radiation that is received by the measuring and reference detectors from substantially the same portion of the material.

The radiations may be electromagnetic radiations, and the source-standardization responses may be derived while directing a beam containing both measuring and reference wavelengths of radiation toward both detectors and substantially filtering out the reference wavelengths from the radiation detected by the measuring detector and substantially filtering out the measuring wavelengths from the radiation detected by the reference detector. The material-condition responses may be derived while directing a beam containing both measuring and reference wavelengths into the material and substantially filtering out the reference wavelengths from the radiation detected by the measuring detector and substantially filtering out the measuring wavelengths from the radiation detected by the reference detector. The radiations may be infrared radiations.

Typically the source radiation produced by the source means includes channel-monitoring wavelengths as well as measuring and reference wavelengths; the measuring and reference wavelengths are substantially filtered out of the source radiation while deriving the monitor-standardization responses and the operation-monitoring responses, and the channel-monitoring wavelengths are substantially filtered out of the source radiation while deriving the source-standardization responses and the material-condition responses.

The monitor-standardization responses and the source-standardization responses may be stored as relatively long-term record values, and each one of the long-term record values may be utilized with a succession of relatively short-term, operation-monitoring response values and material-condition response values to produce a succession of material property responses. The operation-monitoring responses may be stored as relatively short-term record values, and the material property responses may be produced by responding to the long-term record values, the short-term record values and the material-condition responses. Each one of the short-term record values may be utilized with a succession of material-condition response values.

Typically there is formed essentially a ratio of the monitor-standardization responses, and essentially a ratio of the source-standardization responses, and the ratios are stored to produce the long-term record values. A ratio of the operation-monitoring responses may be formed and stored as relatively short-term record values; a ratio of the material-condition response values may be formed, and the material property responses may be produced by responding to the long-term record values, the short-term record values and the ratio of the material-condition response values.

The material property response may be produced substantially in accordance with the relationship expressed by $$f(mp) = \left( \frac{R_{22}}{M_{22}} * k1 * \frac{M_{21}}{R_{21}} * k2 \right) - 1$$

where f(mp) is a function of the material property, $R_{22}$ and $M_{22}$ represent the responses of the respective reference and measuring channels in the operating mode while the detectors receive reference and measuring radiation respectively; k1 is substantially the ratio $M_{12}/R_{12}$ where $M_{12}$ and $R_{12}$ represent the responses of the respective measuring and reference channels in the standardizing mode while the detectors receive measuring and reference radiation respectively; $M_{21}$ and $R_{21}$ represent the responses of the respective measuring and reference channels in the operating mode while both the detectors receive monitoring radiation, and k2 is substantially the ratio $R_{11}/M_{11}$ where $R_{11}$ and $M_{11}$ represent the responses of the respective reference and measuring channels in the standardizing mode while both of the detectors receive monitoring radiation. The quantities k1 and k2 may be produced substantially in accordance with the relationship expressed by $$k1 = A * \frac{M_{12}}{R_{12}} \text{ or } k2 = B * \frac{R_{11}}{M_{11}} \text{ or both,}$$

wherein A and B are constants related to the differences between the geometric conditions of the source means and the detectors in the standardizing mode and in the operating mode.

Typically the amplitude of the response of one of the measuring and reference channels is compared with a predetermined value or range of values; the gain in the one channel is adjusted so that the amplitude of its response is at least approximately the same as the predetermined value or within the range of values, and the other channel is adjusted so that its gain is at least approximately the same as the gain in the one channel. The one channel is typically the reference channel.

The source means and the detectors may be movable relative to the material; the source and detectors may be moved away from the material in the standardizing mode so that the source radiations do not interact substantially with the material, and the source and detectors may be moved adjacent to the material in the operating mode so that the source radiations interact with the material. For determining the properties of a traveling sheet of material, the source means and the detectors may be moved to an off-sheet position to initiate the standardizing mode and moved to an on-sheet position to initiate the operating mode. Where the source means and the detectors are all located on the same side of the material, a standardizing flag may be interposed between the material and the source means and detectors to initiate the standardizing mode.

The objects of this invention are to provide improved methods and means for determining a property of a material utilizing two radiation detectors adapted for simultaneously viewing substantially the same portion of the material and having a channel monitor system that is interrelated with a source standardization system; to provide such methods and means that do not require a high degree of detector stability; to provide such methods and means that do not require high-precision matching of detectors, nor do they require high-precision temperature control of the detectors; to provide such methods and means that do not require well-defined and stable gain in the electronic channels, nor do they require that gain increases or decreases be matched in the two channels; to provide such methods and means that allow the use of dynamically adjustable-gain amplifiers or the like to change the gain as needed, essentially while the measurements are in progress, so as to optimize signal to noise ratios; to provide such methods and means whereby the channel-monitoring radiation can pass through the material being measured, so that a gain change that is suitable for the channel-monitor responses is automatically the same as the gain change that is suitable for the measuring and reference responses; to provide such methods and means wherein the channel-monitoring radiation can be provided by the same source that provides the measuring and/or reference radiation; to provide such methods and means wherein the channel-monitor system can be standardized, and at the same time that source standardization is performed; to provide such methods and means that permit more rapid response while maintaining accuracy when measuring very non-uniform, relatively fast moving materials with dynamically-adjustable gain that is consistent with the non-uniformity of the material; to provide such methods and means adapted for measuring continuously traveling sheet materials with less frequent and less time-consuming trips of the radiation source and detectors to the off-sheet position, and to provide such methods and means that are not dependent on the constancy of internal standard radiation absorbers (filters) for simulating characteristics or changes in the material being measured, nor are they dependent on the precision of mechanical mechanisms for inserting and positioning such filters.

Further objects and advantages of this invention will become apparent in the following detailed description, taken in conjunction with the appended drawings.

BEST MODE FOR CARRYING OUT THE INVENTION

Figure 1:
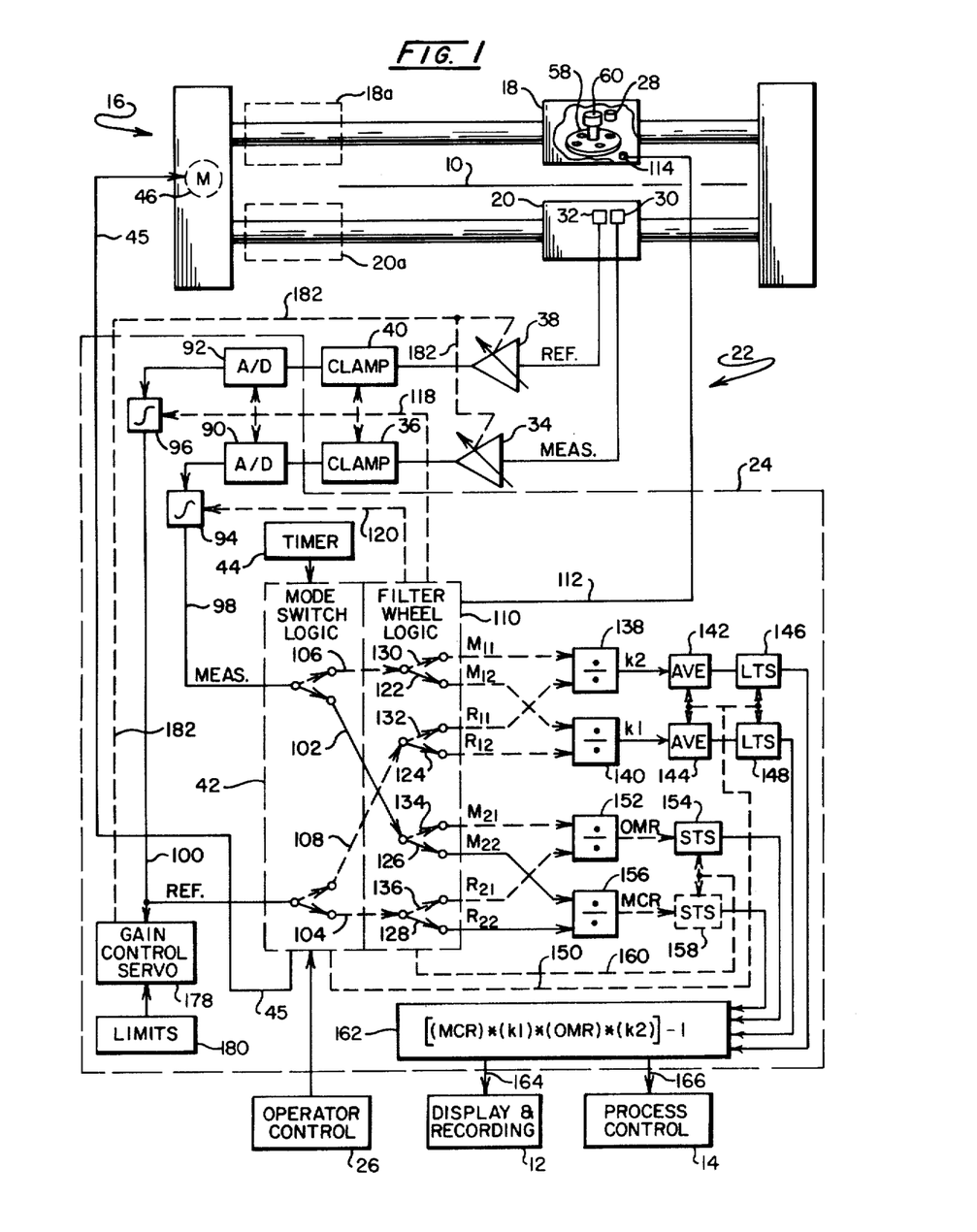
FIG. 1 is a schematic diagram illustrating a typical embodiment of the invention, combining both representations of typical structural elements and representations of typical information-handling procedures.

A typical embodiment of the method and apparatus of this invention is used to determine a property of a sheet material 10, as shown in FIG. 1. It can be imagined that the sheet material 10 is moving out of the paper on which the drawing is made, and toward the viewer. The sheet material 10 is typically a sheet of paper that is traveling from the calender stack to the windup of a paper making machine. The material property to be determined is the paper moisture content. The moisture content values determined by the method and apparatus of the invention are displayed and/or recorded in a known manner by a display and recording device 12. These values are also used in a conventional manner by a process control system 14 to control the paper making machine dryer settings and/or other machine parameters so as to maintain the moisture content of the material 10 at a desired value or values across the width of the sheet.

Physically the illustrative apparatus generally includes a scanner bracket assembly 16 that mounts a radiation source housing 18 and a radiation detector housing 20. The apparatus also includes analog circuitry 22 that forms part of the information channels to be described. The apparatus further includes a computer 24 (enclosed by the heavy dashed line 24) and an operator control 26. The computer 24 typically comprises a digital mini or micro computer of the stored-program type that is conventionally used for sheet process measurement and control purposes. If desired, a suitable analog computer similar to that described in U.S. Pat. No. 4,085,326 supra can also be used.

Referring now to FIG. 1 in more detail, the source housing 18 is adapted to contain source means including a radiation source 28 for producing source radiation including measuring radiation and reference radiation. In the specific embodiment illustrated, the measuring radiation is a narrow band of electromagnetic radiation, specifically infrared radiation having wavelengths around $1.9\mu$ (1.9 microns) while the reference radiation is a narrow band of infrared radiation wavelengths around $1.8\mu$.

The detector housing 20 includes a measuring detector 30 for the measuring radiation and a reference detector 32 for the reference radiation. The measuring detector 30 is part of a measuring information channel that also includes a variable gain amplifier 34, a switched clamp circuit 36, and other components providing functions to be further described. The reference detector 32 is part of a reference information channel that also includes a variable gain amplifier 38, a switched clamp circuit 40, and other components providing functions to be further described.

The source means and the information channels are utilized in both an operating mode and an alternative standardizing mode. The transition from the operating mode to the standardizing mode or vice-versa is effected by conventional mode switch logic represented by a rectangular shaped box 42 enclosed by a heavy dashed line. The transitions are commonly initiated either by operator control 26 or by a timer 44 that may be driven by the usual clock pulse generator (not shown).

One conventional function of the mode switch logic 42 is to provide switching signals, via a line 45 as shown, to a traversing motor 46 that is a part of the scanner bracket assembly 16. On initiation of the standardizing mode, the motor 46 is energized so as to drive the source and detector housings 18 and 20 to their off-sheet positions 18a and 20a so that radiation can pass directly from the source housing to the detector housing without interacting substantially with the sheet material 10. On initiation of the operating mode, the motor 46 is energized to drive the source and detector housings back to an on-sheet position as at 18 and 20. In the operating mode, the radiation detected by detectors 30 and 32 in this particular embodiment is radiation that has passed through, and interacted with, the material of sheet 10.

Figures 2, 4:
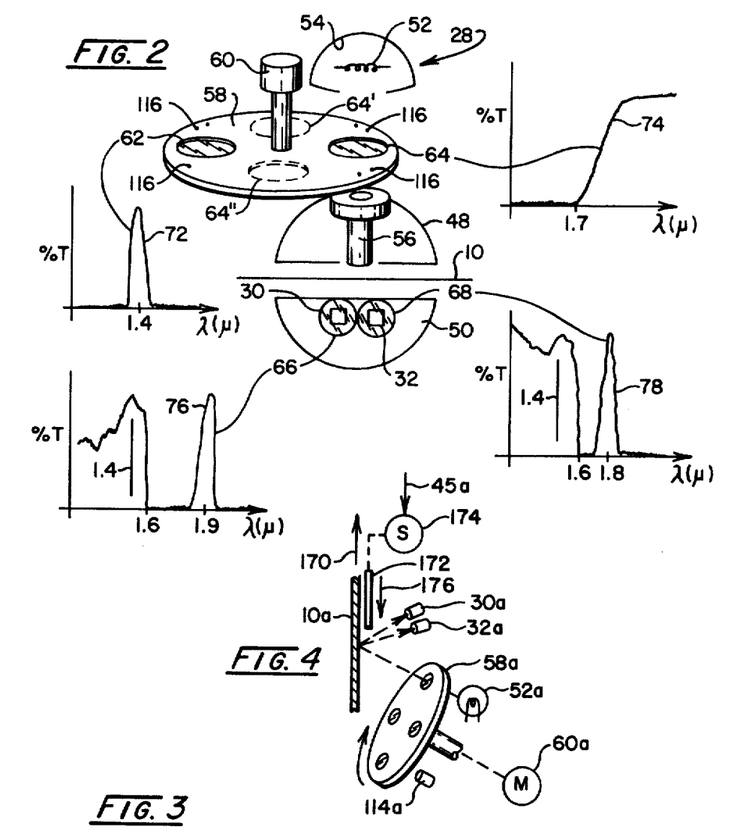
FIG. 2 is a schematic diagram showing in more detail some of the structural elements of FIG. 1 in combination with four graphs depicting the characteristics of radiation filters utilized in the typical embodiment of the invention.
FIG. 4 is a schematic diagram showing a different arrangement of a portion of FIG. 1.

FIG. 2 shows schematically in more detail the structure and the characteristics of the radiation source means and the detector means contained in the source housing 18 and the detector housing 20 of FIG. 1. The optical elements are arranged substantially in accordance with U.S. Pat. No. 4,052,615. An optical cavity is formed between two hemispherical, specular reflectors 48 and 50 that are spaced apart to form a pass gap through which the sheet 10 travels while undergoing measurement. Infrared radiation generated by an incandescent filament 52 is collected by a reflector element 54 and directed to pass through a light pipe collimator 56 that projects a spot of radiation onto the sheet 10 substantially in the center of the cavity formed by reflectors 48 and 50. This radiation is delivered in the form of time-spaced pulses due to the action of a filter wheel 58 that is rotated by a synchronous motor 60.

The FIG. 2 apparatus differs from the apparatus of U.S. Pat. No. 4,052,615 in that different filters as at 62 and 64 are installed in the filter wheel 58; in that two detectors 30 and 32 instead of one are provided in the lower hemisphere 50, and in that the measuring detector 30 and the reference detector 32 are covered by respective filters 66 and 68.

Associated with each filter in FIG. 2 is a graph showing percent transmission (%T) as a function of the wavelength ($\lambda$) of the radiation given in microns ($\mu$). Thus a graph 72 is associated with filter 62; a graph 74 is associated with filter 64; a graph 76 is associated with filter 66, and a graph 78 is associated with filter 68.

Filter 62 is a narrow band filter that passes a narrow band of radiation around 1.4 microns. This radiation provides an example of what is herein termed channel-monitoring radiation. Filter 64 is a long wave pass filter that substantially attenuates or blocks the passage of wavelengths shorter than about 1.7 microns while substantially transmitting the longer wavelengths. The filter 66 has the characteristics of a Fabry-Perot interference filter, passing a narrow band of wavelengths around 1.9 microns and also passing as a sideband the short wavelengths less than about 1.6 microns. The narrow band around 1.9 microns provides an example of what is herein termed measuring radiation. It is selectively absorbed, through the process of molecular resonance absorption, by the water contained in the paper sheet material 10. Filter 68 is similar to filter 66, except that instead of passing the band around 1.9 microns, it passes a narrow band of wavelengths around 1.8 microns. The latter radiation is not selectively absorbed by the constituents of the sheet material. This radiation provides an example of what is herein termed reference radiation.

To summarize the cooperation of the filters, when filter 62 is located between the source lamp assembly 28 and light pipe assembly 56, both detectors 30 and 32 receive the 1.4 micron channel-monitoring radiation from the source, with other wavelengths being substantially blocked. When the filter wheel 58 rotates to place filter 64 in the same location, as shown, the measuring detector 30 receives the 1.9 micron measuring radiation, with other wavelengths being substantially blocked. At the same time, the reference detector 32 receives the 1.8 micron reference radiation, with other wavelengths being substantially blocked.

Figure 3:
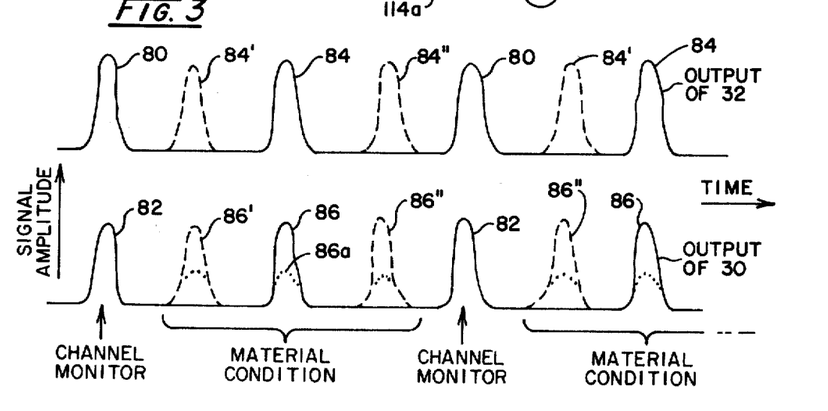
FIG. 3 is a sketch of typical waveforms representing detector signal amplitudes as a function of time.

FIG. 3 shows waveforms representing typical output signals provided by detectors 30 and 32 when the material 10 is passing through the gap between hemispheres 48 and 50. Proceeding from left to right in time sequence, the pulses 80 and 82 are operation-monitoring pulses derived simultaneously from the reference 32 and measuring 30 detectors respectively, in response to the 1.4 micron channel monitoring radiation. Pulses 84 and 86 are material-condition pulses. Pulse 84 is produced by the reference radiation detector 32 in response to the 1.8 micron reference radiation passing through filters 64 and 68. Pulse 86 is produced by the measuring radiation detector 30 in response to the 1.9 micron measuring radiation passing through filters 64 and 66. Pulses 84 and 86 occur simultaneously. Pulses 84 and 86 are followed by a recurrence of pulses 80 and 82, which are in turn followed by a recurrence of pulses 84 and 86, and so on.

Typically the radiations are selected where possible so that the non-selective absorption processes occurring in the material 10 produce about the same attenuation of the channel-monitoring, reference and measuring radiations. Thus the solid line pulses shown at 80, 82, 84 and 86 all have about the same amplitude. The 1.9 micron measuring radiation, however, is selectively absorbed by the moisture in the paper sheet 10 so that the associated measuring radiation detector pulses will typically be attenuated to a lesser value such as that shown by the dotted line 86a. That is to say, as the material 10 varies from bone dry to moist, the amplitude of the measuring pulse will vary from 86 to 86a, whereas the amplitude of the reference pulse 84 will not be substantially affected by the variation in moisture content. As in most conventional instruments, basically the moisture content is determined as a function of the ratio of the amplitudes of pulses 86a and 84.

Optionally, the dashed-line pulses 84', 86', 84" and 86" may be produced if desired by installing additional filters 64' and 64" in filter wheel 58 as indicated by the dashed lines. The filters 64' and 64" may be similar or identical to filter 64. The use of the additional filters triples the sampling rate and is appropriate where necessary to increase the signal to noise ratio and/or to provide faster response.

Referring again to FIG. 1, as previously noted the measuring detector 30 is a component of a measuring information channel that includes a variable gain amplifier 34 and a switched clamp circuit 36. Similarly, the reference detector 32 is a component of a reference information channel that includes a variable gain amplifier 38 and a switched clamp circuit 40. The analog pulse signals appearing at the outputs of clamp circuits 36 and 40 are converted to digital signals as indicated at 90 and 92 and digitally integrated as indicated at 94 and 96. Clamp circuits 36 and 40 are typically of the kind described in U.S. Pat. No. 4,085,326 supra. The pulses at the output of the clamp circuits 36 and 40 resemble the pulses illustrated by the waveforms in FIG. 3. The duration of each pulse as at 80 from zero level to zero level is typically about two milliseconds and a typical analog to digital (A/D) conversion performed on each pulse signal takes place about every twenty-five microseconds. A line 98 represents a portion of the measuring information channel that receives a digital value for the amplitude of each pulse as at 82 that has been integrated as indicated at 94. Similarly a line 100 represents a portion of the reference information channel that receives a digital value for the amplitude of each pulse as at 80 that has been integrated as indicated at 96.

The measuring and reference information channel values on lines 98 and 100 are each shown to be routed along alternate paths by the mode switch logic 42. Thus in the operating mode, for example when the source and detector housings 18 and 20 are on sheet as shown, the respective measuring and reference channel values on lines 98 and 100 are shown to be transmitted along lower solid line paths 102 and 104. In the standardizing mode, for example when the housings are off sheet as shown at 18a and 20a, the values on lines 98 and 100 are transmitted along the upper dashed line paths 106 and 108 as shown.

Additional alternate routing of the values derived from the measuring and reference information channels is provided by conventionally designed filter wheel logic shown to be enclosed by a heavy dashed line 110. Typically the filter wheel logic system 110 responds to pulse signals on a line 112 from a magnetic reluctance sensor 114 (or other appropriate sensor) that detects the passing of small iron "logic slugs" as shown at 116 in FIG. 2 (or other appropriate indicia) around the periphery of the filter wheel 58. Logic system 110 uses the pulse signals to maintain continually updated information on the instantaneous position of the filter wheel 58. In accordance with the filter wheel position, and as indicated by the dotted lines 118 and 120, the logic system 110 controls the timing of the switched clamp circuit 36 and 40 functions, the analog to digital conversions at 90 and 92 and the time limits of the digital integrations performed at 94 and 96.

The values on lines 98 and 100, derived from the information channels and selectively routed through alternate paths 102, 104, 106 and 108 by the mode switch logic system 42, are subject to the additional alternate routing, in dependence on the filter wheel position, and again in accordance with conventional demultiplexer techniques. When the filter wheel 58 is in the position shown in FIG. 2, for example, placing the long wave pass filter 64 in the path of radiation from source 52 to detectors 30 and 32, the lower, solid line paths 122, 124, 126 and 128 as shown are enabled. When the channel-monitoring band pass filter 62 is in the radiation path, for example, the filter wheel logic 110 will have disabled paths 122, 124, 126 and 128 and enabled the alternate, upper dashed line paths shown at 130, 132, 134 and 136 instead.

The functioning of the portions of the embodiment of the invention so far shown and described can now be summarized as follows:

In the standardizing mode, a monitor-standardization response is derived from each of the two channels while passing monitoring radiation to both detectors. In FIG. 1, the monitor-standardization response derived from the measuring channel is identified as $M_{11}$ while that derived from the reference channel is identified as $R_{11}$.

Also in the standardizing mode, a source-standardization response is derived from each of the two channels while passing measuring radiation (e.g., 1.9 microns) to the measuring detector 30 and passing reference radiation (e.g., 1.8 microns) to the reference detector 32. In FIG. 1, the measuring channel response so derived is identified as $M_{12}$ while the reference channel response is identified as $R_{12}$.

In the operating mode, an operation-monitoring response is derived from each of the two channels while passing monitoring radiation to both detectors. In FIG. 1, the measuring channel response so derived is identified as $M_{21}$ while the reference channel response is identified as $R_{21}$.

Also in the operating mode, a material-condition response is derived from each of the two channels while directing source radiation into the material, and passing to the respective measuring 30 and reference 32 detectors measuring and reference radiation that has interacted with the material 10. In FIG. 2 the measuring channel response so derived is identified as $M_{22}$ while the reference channel response is identified as $R_{22}$.

In the FIG. 1 system for identifying the responses, the letter designation M indicates that the response is derived from the measuring information channel, while the letter designation R indicates that the response is derived from the reference information channel. In the first subscript number following the letter designation, the numeral 1 indicates that the response is derived in the standardizing mode, while the numeral 2 indicates that the response is derived in the operating mode. In the second subscript number following the letter designation, the numeral 1 indicates that the response is derived while the detector is receiving channel-monitoring radiation, while the numeral 2 indicates that the detector is receiving measuring or reference radiation. When the last subscript number is a 2, the specific kind of radiation involved can be determined from the letter designation, since the measuring detector 30 adapted to detect the measuring radiation is a component of the measuring (M) channel whereas the reference detector 32 adapted to detect the reference radiation is a component of the reference (R) channel.

Other portions of the embodiment of the invention to be described hereinafter function to respond to the monitor-standardization responses $M_{11}$ and $R_{11}$, the source-standardization responses $M_{12}$ and $R_{12}$, the operation-monitoring responses $M_{21}$ and $R_{21}$ and the material-condition responses $M_{22}$ and $R_{22}$ so as to produce a material property (e.g., moisture content) response that is effectively standardized and substantially independent of changes in the gain of either one or both of the measuring and reference information channels.

To this end, typically a quantity k2 that is substantially the ratio of the responses $R_{11}$ and $M_{11}$ is formed as indicated at 138. Similarly a quantity k1 that is substantially the ratio of the responses $M_{12}$ and $R_{12}$ is formed as indicated at 140. Typically k2 and k1 are derived during a standardization interval, determined by the setting of timer 44, that occurs once about every 30 to 60 minutes and lasts for about one-half minute. During this half minute, as filter wheel 58 rotates, typically a k2 value and a k1 value are obtained once about every 8 milliseconds and the values are averaged as indicated at 142 and 144 over a substantial portion of the half-minute interval, for example, while the source and detector housings are off-sheet as at 18a and 20a.

The monitor-standardization responses $M_{11}$ and $R_{11}$ and the source-standardization responses $M_{12}$ and $R_{12}$ are derived during the half-minute standardization interval and cannot ordinarily be derived during the remaining twenty-nine minutes when the operating mode prevails in the operation of the illustrative embodiment. Hence the monitor-standardization and the source-standardization responses are stored, conveniently in the form of the averaged values of the ratios k2 and k1, as relatively long-term record values placed in storage as indicated in 146 and 148. In the context of the specific illustrative embodiment, "long-term" as applied to the record values or their long-term storage (LTS) refers to a period of time that is long relative to the period of filter wheel 58 rotation, or more specifically about 30 to 60 minutes. Where appropriate, long-term periods of ten or fifteen minutes, or other fixed or variable intervals related, say, to the scanning time of the source and detector housings 18 and 20 across the sheet 10, or to certain operating parameters of the sheet-making process, may be conventionally established as needed by the mode switch logic system 42. Such control of the averaging 142 and 144 and long-term storage 146 and 148 is indicated by the dotted lines as at 150.

The operation-monitoring responses $M_{21}$ and $R_{21}$ are derived during the operating mode, for example, when the source and detector housings 18 and 20 are on sheet and the detectors 30 and 32 receive radiation that has interacted with, or more specifically, passed through, the material 10 in the illustrated embodiment. The ratio of the responses $M_{21}$ and $R_{21}$ is formed as indicated at 152. For convenience in the drawing, the ratio is identified as OMR (operation-monitor ratio). Its value is conveniently stored as a relatively short-term record value in short-term storage (STS) as indicated at 154.

The ratio of the material-condition responses $M_{22}$ and $R_{22}$ is conveniently formed as indicated at 156. For convenience in the drawing, this ratio is identified as MCR (the material-condition ratio). Optionally the MCR may be stored in short-term storage (STS) as indicated at 158 or it may be directly utilized with the information stored at 146, 148 and 154.

"Short-term" as applied to the storage operations at 154 and 158 in the illustrative embodiment means that the term is short relative to the time between standardization intervals and may last for only one rotation period of the filter wheel 58. Of course, any desired and reasonable number of OMR and MCR values may be averaged to form the short-term record values placed in storage at 154 and 158. Appropriately, the storage functions at 154 and 158, as well as any associated averaging functions (not shown) are controlled by the filter wheel logic system 110 as indicated by the dotted lines 160.

The end result of the method and apparatus depicted in FIGS. 1 and 2 is the production of a material property response, here exemplified as a response to the moisture content of material 10. This response is shown to be produced at 162 by the computer 24, utilizing the k2, k1, OMR and MCR values in the computation shown. The material property response is shown to be delivered as an output on a line 164 to display and recording unit 12. The same or a similar output is shown to be delivered via a line 166 to the process control unit 14.

Each one of the long term record values stored as at 146 and 148 is typically used with a succession of short-term operation-monitoring response values (e.g., OMR values) and material condition response values (e.g., MCR values) to produce a succession of material property responses. Typically also, particularly when the optional filters 64' and 64" of FIG. 2 are used and the additional material-condition pulses 84', 86', 84" and 86" of FIG. 3 are derived, each short-term record value (e.g., OMR value) stored as at 154 may be used with a succession of material condition response values (e.g., MCR values).

By substituting into the mathematical expression shown at 162 the equivalent values of MCR and OMR it is seen that the response at 164 (or at 166) is a function f(mp) of the material property in accordance with $$f(mp) = \left( \frac{R_{22}}{M_{22}} * k1 * \frac{M_{21}}{R_{21}} * k2 \right) - 1. \tag{2}$$

Here the product $R_{22}/M_{22} * k1$ can be termed the standardized material condition ratio and the product $M_{21}/R_{21} * k2$ can be termed the standardized monitor ratio.

Further expanding equation (2) by substituting the equivalent values of k1 and k2 produces $$f(mp) = \left( \frac{R_{22}}{M_{22}} * \frac{M_{12}}{R_{12}} * \frac{M_{21}}{R_{21}} * \frac{R_{11}}{M_{11}} \right) - 1. \tag{3}$$

From equation (3) it can be seen that when a gain change $g_1$ occurs in the reference channel during the operating mode, the gain change acts as a multiplier in the numerator of the material condition ratio and also as the same multiplier in the denominator of the operating monitor ratio, thus $$f(mp) = \left( \frac{g_1 R_{22}}{M_{22}} * \frac{M_{12}}{R_{12}} * \frac{M_{21}}{g_1 R_{21}} * \frac{R_{11}}{M_{11}} \right) - 1 \quad (4)$$

so that the value of the material property response f(mp) remains constant. Similarly if a gain change $g_2$ occurs in the measuring channel during the operating mode, the gain change acts as a multiplier in the denominator of the material condition ratio and also as the same multiplier in the numerator of the operating monitor ratio, thus $$f(mp) = \left( \frac{R_{22}}{g_2 M_{22}} * \frac{M_{12}}{R_{12}} * \frac{g_2 M_{21}}{R_{21}} * \frac{R_{11}}{M_{11}} \right) - 1 \quad (5)$$

so that the value of the material property response f(mp) again remains constant.

For similar reasons it can be seen that gain changes occurring during standardization likewise have no substantial effect on the material property response. Referring to any one of equations (3), (4) or (5) and with reference to FIG. 3 (the solid line waveforms are very much the same as the waveforms occurring during standardization) it is apparent that samples of both the reference channel responses $R_{12}$ and $R_{11}$ are taken within one period of revolution of the filter wheel 58, (e.g., eight milliseconds) and the same is true for samples of both measuring channel responses $M_{12}$ and $M_{11}$. Since the standardization ratios k1 and k2 are averages of a great many samples of these responses, k1 and k2 are in effect derived at the same time, and any gain change occurring in either channel affects both ratios k1 and k2 equally in the reciprocal sense. Hence the gain changes do not affect the value of the product k1 * k2 or the value of the material property response f(mp).

The calibration of the instrument is commonly based on a function or curve that can be plotted graphically, relating values of f(mp) to corresponding moisture content values obtained by laboratory techniques. Theoretically the value of f(mp) is zero when the moisture content is zero, as well as when the sheet material 10 is absent, as in standardization. However, it is frequently found that when the actual curve of f(mp) versus moisture content is extrapolated to zero moisture content, the value of f(mp) is not zero. This is due to the fact that the geometric conditions of the source means and the detectors are different in the standardizing mode and in the operating mode. In the FIG. 1 and FIG. 2 arrangement, for example, there may be certain radiation scattering conditions in the region of the pass gap between the source means and the detectors that are different when the sheet 10 is present and when it is absent. To correct for the effect of this discrepancy, an adjustment may be made to the value of k1 such that $$k1 = A * \frac{M_{12}}{R_{12}}$$

where A is a constant so selected that f(mp) is zero for zero moisture content or other material property.

In a similar manner, provisions should be made for an adjustment to the value of k2 such that $$k2 = B * \frac{R_{11}}{M_{11}}.$$

The constant B provides a form of compensation that is most frequently needed in a reflection gauge such as that whose elements are shown schematically in FIG. 4. The parts whose reference numerals have the suffix "a" correspond to parts in FIGS. 1 and 2.

In FIG. 4 a material 10a which may be a blown film of plastic moving in the direction of the arrow 170, is measured by directing radiation from a source 52a through filters in a filter wheel 58a into one surface of the material 10a and detecting the radiation reflected from the material onto detectors 30a and 32a on the same side of the material. In this case, no provision is made for moving the source and detector housings (not shown) off sheet. Instead, there is provided a standardizing flag 172 adapted to be interposed between the material 10a and the source means and detectors, so that the detectors 30a and 32a, instead of receiving radiation that has interacted with the material, receive radiation reflected from the flag 172.

When standardization is initiated, the mode switch logic 42, FIG. 1, will provide a signal on a line 45a for energizing an electrical solenoid 174 or similar motor to move the standardizing flag in the direction of the arrow 176 so that the flag is interposed between the material 10a and the source means and detectors. The constant B compensates for the effect, of the difference between the plane of the standardizing flag and the plane of the material, on the signals as a result of any non-uniformity of the radiation beam or fields of view of the detectors. The constants A and B may be stored in the memory (not shown) of computer 24 and used to modify the computation shown at 162. If computer 24 is an analog computer, the constants A and B can be stored and utilized in a manner similar to that described in U.S. Pat. No. 4,085,326 supra for compensating for the same geometric condition variations.

The achievement of a material property response that is effectively standardized and substantially independent of information channel gain permits the use of dynamically adjustable gain that is automatically variable in response to signal level changes at any time, in either the operating mode or in the standardizing mode. Accordingly as shown in FIG. 1 the computer 24 implements, in a conventional manner, the function of a gain control servo as indicated at 178.

The servo 178 monitors the amplitude of the digital signal that appears as indicated on line 100 in the reference information channel, by comparing it with amplitude limit values indicated at 180 that may be stored in the computer memory. The gain of the AGC amplifiers 34 and 38 in each of the measuring and reference channels is incrementally adjustable and set by digital signals applied as indicated over lines 182 from the servo 178. For a given digital gain control signal, the gains of the AGC amplifiers 34 and 38 are determined within ordinary commercial tolerances of about five percent, which is quite adequate in view of the gain independence of the measurement. The gain control servo 178 thus adjusts the gain in the one channel (the reference channel) so that the amplitude of its response is at least approximately the same as the predetermined value or range of values used as limits 180. Since the same digital gain setting signal is transmitted via lines 182 to both AGC amplifiers 34 and 38, the other channel (the measuring channel) is adjusted so that its gain is at least approximately the same as the gain in the one channel.

The ability to use dynamically and automatically adjustable-gain amplifiers such as amplifiers 34 and 38 at the "front end" of the system, where signal to noise ratios are very important, it particularly advantageous for measurements such as infrared transmission measurements on heavy paper board. Here a dynamic range of detector signals as high as 72 db have been encountered.

This example also points out the advantages of using a channel-monitoring radiation source means that is arranged to direct the channel-monitoring radiation into the material in the operating mode and deriving the operation-monitoring responses in response to channel-monitoring radiation received by the detectors from the material. It is apparent, for example, that the invention could be practiced with a separate source of channel-monitoring radiation located on the same side of the material 10 with the detectors 30 and 32. In such an arrangement, the filter wheel position of filter 62, FIG. 2 could be opaque, and a light-emitting diode (LED) could be flashed on and off at appropriate times by the filter wheel logic system 110. The LED would be located in hemisphere 50 and would be arranged so as to pass its light pulses equally and simultaneously to both detectors 30 and 32, either directly or through filters 66 and 68.

However, the gain control problem with such an arrangement becomes apparent in consideration of the heavy paper board example, since the channel-monitoring radiation pulses would have a relatively constant amplitude, whereas the interspersed measuring radiation pulses received through the material would be subject to the 72-db amplitude variation. This problem is greatly alleviated in the best mode embodiment described above since the channel monitoring radiation pulses as well as the reference and measuring radiation pulses are attenuated by the sheet 10.

In the embodiments of the invention above described, the channel-monitor, reference and measuring wavelengths are all different because of the filter techniques used to pass the radiations to the proper detectors at the proper time. It is contemplated, however, that in some cases the channel-monitor radiation could be the same as the reference radiation, for example, if a satisfactory way can be found to pass the radiations to the proper detectors at the proper times without interference of the signals and without interference from the effects of ambient radiation, say, which effects could be produced if the ambient radiation reaching the detectors is chopped by a rotating chopper, filter wheel or the like.

While the invention has been described and illustrated by particular procedures and particular apparatus, the showing and description is meant to be illustrative only and not restrictive, since many changes and modifications can be made without departing from the spirit and scope of the invention.

What is claimed is:

1. A method for determining a property of a material, utilizing source means for producing source radiation including measuring radiation and reference radiation, a measuring information channel including a detector for the measuring radiation, and a reference information channel including a detector for the reference radiation, the source means and the information channels being utilized in both an operating mode and an alternative standardizing mode, the method comprising producing a channel-monitoring radiation;

in the standardizing mode, deriving a monitor-standardization response from each of the two channels while passing monitoring radiation to both detectors;

in the standardizing mode, deriving a source-standardization response from each of the two channels while passing measuring radiation to the measuring detector and passing reference radiation to the reference detector;

in the operating mode, deriving an operation-monitoring response from each of the two channels while passing monitoring radiation to both detectors;

in the operating mode, deriving a material-condition response from each of the two channels while directing source radiation into the material, and passing to the respective measuring and reference detectors measuring and reference radiation that has interacted with the material, and responding to the monitor-standardization responses, the source-standardization responses, the operation-monitoring responses and the material-condition responses so as to produce a material property response that is effectively standardized and substantially independent of gain changes occurring in either one or both of the measuring and reference information channels.

2. A method as in claim 1 wherein the channel-monitoring radiation is directed into the material in the operating mode, and wherein the operation-monitoring responses are derived in response to channel-monitoring radiation that is received by the detectors from the material.

3. A method as in claim 2 wherein the channel-monitoring radiation is directed into the material from one side thereof and wherein the detectors receive the monitoring radiation from the opposite side.

4. A method as in claim 2 wherein the channel-monitoring radiation is directed into the material from one side thereof, and the monitoring radiation reflected from the material is detected on the same side.

5. A method as in claim 2 wherein the channel-monitoring radiation is produced by the source means that produces the source radiation.

6. A method as in claim 1 wherein the measuring and reference radiation, that is passed to the respective measuring and reference detectors in order to derive the material-condition responses, is radiation that has interacted with the material in substantially the same portion thereof.

7. A method as in claim 6 wherein the channel-monitoring radiation is directed into the material in the operating mode, and wherein the operation-monitoring responses are derived in response to monitoring radiation that is received by the measuring and reference detectors from substantially the same portion of the material.

8. A method as in claim 1 wherein the radiations are electromagnetic radiations;

wherein the source-standardization responses are derived while directing a beam containing both measuring and reference wavelengths of radiation toward both detectors and substantially filtering out the reference wavelengths from the radiation detected by the measuring detector and substantially filtering out the measuring wavelengths from the radiation detected by the reference detector, and wherein the material-condition responses are derived while directing a beam containing both measuring and reference wavelengths into the material and substantially filtering out the reference wavelengths from the radiation detected by the measuring detector and substantially filtering out the measuring wavelengths from the radiation detected by the reference detector.

9. A method as in claim 8 wherein the radiations are infrared radiations.

10. A method as in claim 8 wherein the source radiation produced by the source means includes channel-monitoring wavelengths as well as measuring and reference wavelengths;

wherein the measuring and reference wavelengths are substantially filtered out of the source radiation while deriving the monitor-standardization responses and the operating-monitoring responses, and wherein the channel-monitoring wavelengths are substantially filtered out of the source radiation while deriving the source-standardization responses and the material-condition responses.

11. A method as in claim 10 wherein the radiations are infrared radiations.

12. A method as in claim 1 that comprises storing the monitor-standardization responses and the source-standardization responses as relatively long-term record values, and utilizing each one of the long-term record values with a succession of relatively short-term, operation-monitoring response values and material-condition response values to produce a succession of material property responses.

13. A method as in claim 12 that comprises storing the operation-monitoring responses as relatively short-term record values, and producing the material property responses by responding to the long-term record values, the short-term record values and the material-condition responses.

14. A method as in claim 13 that comprises utilizing each one of the short-term record values with a succession of material-condition response values.

15. A method as in claim 13 that comprises forming essentially a ratio of the monitor-standardization responses, forming essentially a ratio of the source-standardization responses, and storing the ratios to produce the long-term record values.

16. A method as in claim 15 that comprises forming a ratio of the operation-monitoring responses storing the ratio of the operation-monitoring responses as relatively short-term record values, forming a ratio of the material-condition response values, and producing the material property responses by responding to the long-term record values, the short-term record values and the ratio of the material-condition response values.

17. A method as in claim 12 wherein the radiations are infrared radiations.

18. A method as in claim 1 wherein the material property response is produced substantially in accordance with the relationship expressed by $$f(mp) = \left( \frac{R_{22}}{M_{22}} * k1 * \frac{M_{21}}{R_{21}} * k2 \right) - 1$$

where f(mp) is a function of the material property, $R_{22}$ and $M_{22}$ represent the responses of the respective reference and measuring channels in the operating mode while the detectors receive reference and measuring radiation respectively; k1 is substantially the ratio $M_{12}/R_{12}$ where $M_{12}$ and $R_{12}$ represent the responses of the respective measuring and reference channels in the standardizing mode while the detectors receive measuring and reference radiation respectively; $M_{21}$ and $R_{21}$ represent the responses of the respective measuring and reference channels in the operating mode while both of the detectors receive monitoring radiation, and k2 is substantially the ratio $R_{11}/M_{11}$ where $R_{11}$ and $M_{11}$ represent the responses of the respective reference and measuring channels in the standardizing mode while both of the detectors receive monitoring radiation.

19. A method as in claim 18 wherein $$k1 = A * \frac{M_{12}}{R_{12}} \text{ or } k2 = B * \frac{R_{11}}{M_{11}} \text{ or both,}$$

and wherein A and B are constants related to the differences between the geometric conditions of the source means and the detectors in the standardizing mode and in the operating mode.

20. A method as in claim 1 which comprises comparing the amplitude of the response of one of the measuring and reference channels with a predetermined value or range of values, adjusting the gain in the one channel so that the amplitude of its response is at least approximately the same as the predetermined value or within the range of values, and adjusting the other channel so that its gain is at least approximately the same as the gain in the one channel.

21. A method as in claim 20 wherein the one channel is the reference channel.

22. A method as in claim 1 wherein the source means and the detectors are movable relative to the material, which comprises moving the source and detectors away from the material in the standardizing mode so that the source radiations do not interact substantially with the material and moving the source and detectors adjacent to the material in the operating mode so that the source radiations interact with the material.

23. A method as in claim 22 for determining the properties of a traveling sheet of material, wherein the source means and the detectors are moved to an off-sheet position to initiate the standardizing mode and moved to an on-sheet position to initiate the operating mode.

24. A method as in claim 1 wherein the source means and the detectors are all located on the same side of the material, which comprises interposing a standardizing flag between the material and the source means and detectors to initiate the standardizing mode.

25. Apparatus for determining a property of a material, comprising source means for producing source radiation including measuring radiation and reference radiation, a measuring information channel including a detector for the measuring radiation, a reference information channel including a detector for the reference radiation, means for putting the source means and the information channels in an operating mode and for putting them alternatively in a standardizing mode, means for producing a channel-monitoring radiation, means effective in the standardizing mode for deriving a monitor-standardization response from each of the two channels while passing monitoring radiation to both detectors, means effective in the standardizing mode for deriving a source-standardization response from each of the two channels while passing measuring radiation to the measuring detector and passing reference radiation to the reference detector;

means effective in the operating mode for deriving an operation-monitoring response from each of the two channels while passing monitoring radiation to both detectors;

means effective in the operating mode for deriving a material-condition response from each of the two channels while directing source radiation into the material and passing to the respective measuring and reference detectors measuring and reference radiation that has interacted with the material, and means responsive to the monitor-standardization responses, the source-standardization responses, the operation-monitoring responses and the material-condition responses for producing a material property response that is effectively standardized and substantially independent of gain changes occurring in either one or both of the measuring and reference information channels.

26. Apparatus as in claim 25 comprising means for directing the channel-monitoring radiation into the material in the operating mode, and wherein the means for deriving the operation-monitoring responses is responsive to channel-monitoring radiation that is received by the detectors from the material.

27. Apparatus as in claim 26 wherein the means for directing the channel-monitoring radiation is adapted to direct it into the material from one side thereof and wherein the detectors are adapted to receive the monitoring radiation from the opposite side.

28. Apparatus as in claim 26 wherein the means for directing the channel-monitoring radiation is adapted to direct it into the material from one side thereof, and the detectors are adapted to detect the monitoring radiation reflected from the material on the same side.

29. Apparatus as in claim 26 wherein the source means that produces the source radiation also produces the channel-monitoring radiation.

30. Apparatus as in claim 25 wherein the measuring and reference radiation, that is passed to the respective measuring and reference detectors in order to derive the material-condition responses, is radiation that has interacted with the material in substantially the same portion thereof.

31. Apparatus as in claim 30 comprising means for directing the channel-monitoring radiation into the material in the operating mode, and wherein the means for deriving the operation-monitoring responses is responsive to monitoring radiation that is received by the measuring and reference detectors from substantially the same portion of the material.

32. Apparatus as in any one of claims 25, 29, 30 or 31 wherein the radiations are electromagnetic radiations;

wherein the means for deriving the source-standardization responses is adapted to derive them while directing a beam containing both measuring and reference wavelengths of radiation toward both detectors and substantially filtering out the reference wavelengths from the radiation detected by the measuring detector and substantially filtering out the measuring wavelengths from the radiation detected by the reference detector, and wherein the means for deriving the material-condition responses derives them while directing a beam containing both measuring and reference wavelengths into the material and substantially filtering out the reference wavelengths from the radiation detected by the measuring detector and substantially filtering out the measuring wavelengths from the radiation detected by the reference detector.

33. Apparatus as in claim 32 wherein the radiations are infrared radiations.

34. Apparatus as in claim 32 wherein the source means produces source radiation including channel-monitoring wavelengths as well as measuring and reference wavelengths, comprising means for substantially filtering the measuring and reference wavelengths out of the source radiation while the monitor-standardization responses and the operation-monitoring responses are derived, and means for substantially filtering the channel-monitoring wavelengths out of the source radiation while the source-standardization responses and the material-condition responses are derived.

35. Apparatus as in claim 34 wherein the radiations are infrared radiations.

36. Apparatus as in any one of claims 25, 26, 29, 30 or 31 that comprises means for storing the monitor-standardization responses and the source-standardization responses as relatively long-term record values, and for utilizing each one of the long-term record values with a succession of relatively short-term, operation-monitoring response values and material-condition response values to produce a succession of material property responses.

37. Apparatus as in claim 36 wherein the storing and utilizing means stores the operation-monitoring responses as relatively short-term record values, and produces the material property responses by responding to the long-term record values, the short-term record values and the material-condition responses.

38. Apparatus as in claim 37 wherein the storing and utilizing means is adapted to utilize each one of the short-term record values with a succession of material-condition response values.

39. Apparatus as in claim 37 wherein the storing and utilizing means is adapted to form essentially a ratio of the monitor-standardization responses, form essentially a ratio of the source-standardization responses, and store the ratios to produce the long-term record values.

40. Apparatus as in claim 39 wherein the storing and utilizing means is adapted to form a ratio of the operation-monitoring responses, store the ratio of the operation-monitoring responses as relatively short-term record values, form a ratio of the material-condition response values, and produce the material property responses by responding to the long-term record values, the short-term record values and the ratio of the material-condition response values.

41. Apparatus as in claim 36 wherein the radiations are infrared radiations.

42. Apparatus as in claim 25, 26, 29, 30 or 31 wherein the means for producing the material property response produces it substantially in accordance with the relationship expressed by $$f(mp) = \left( \frac{R_{22}}{M_{22}} * k1 * \frac{M_{21}}{R_{21}} * k2 \right) - 1$$

where f(mp) is a function of the material property, $R_{22}$ and $M_{22}$ represent the responses of the respective reference and measuring channels in the operating mode while the detectors receive reference and measuring radiation respectively; k1 is substantially the ratio $M_{12}/R_{12}$ where $M_{12}$ and $R_{12}$ represent the responses of the respective measuring and reference channels in the standardizing mode while the detectors receive measuring and reference radiation respectively; $M_{21}$ and $R_{21}$ represent the responses of the respective measuring and reference channels in the operating mode while both of the detectors receive monitoring radiation, and k2 is substantially the ratio $R_{11}/M_{11}$ where $R_{11}$ and $M_{11}$ represent the responses of the respective reference and measuring channels in the standardizing mode while both of the detectors receive monitoring radiation.

43. Apparatus as in claim 42 wherein $$k1 = A * \frac{M_{12}}{R_{12}} \text{ and } k2 = B * \frac{R_{11}}{M_{11}}$$

and wherein A and B are constants related to the differences between the geometric conditions of the source means and the detectors in the standardizing mode and in the operating mode.

44. Apparatus as in any one of claims 25, 26, 29, 30 or 31 which comprises means for comparing the amplitude of the response of one of the measuring and reference channels with a predetermined value or range of values, means for adjusting the gain in the one channel so that the amplitude of its response is at least approximately the same as the predetermined value or within the range of values, and means for adjusting the other channel so that its gain is at least approximately the same as the gain in the one channel.

45. Apparatus as in claim 44 wherein the one channel is the reference channel.

46. Apparatus as in any one of claims 25, 26, 29, 30 or 31 wherein the source means and the detectors are movable relative to the material, which comprises means for moving the source and detectors away from the material in the standardizing mode so that the source radiations do not interact substantially with the material and for moving the source and detectors adjacent to the material in the operating mode so that the source radiations interact with the material.

47. Apparatus as in claim 46 for determining the properties of a traveling sheet of material, wherein the source and detector moving means is adapted to move the source and detectors to an off-sheet position to initiate the standardizing mode and to move them to an on-sheet position to initiate the operating mode.

48. Apparatus as in any one of claims 25, 28, 29, 30 or 31 wherein the source means and the detectors are all located on the same side of the material, which comprises a standardizing flag and means for interposing the standardizing flag between the material and the source means and detectors to initiate the standardizing mode.

* * * * *